US005885972A

United States Patent [19]
Weis et al.

[11] Patent Number: 5,885,972
[45] Date of Patent: Mar. 23, 1999

[54] L-PYRANOSYL NUCLEOSIDES

[75] Inventors: Alexander L. Weis, San Antonio, Tex.; Charles T. Goodhue, Rochester, N.Y.

[73] Assignee: Genencor International, Inc., Rochester, N.Y.

[21] Appl. No.: 720,853

[22] Filed: Oct. 2, 1996

Related U.S. Application Data

[63] Continuation of Ser. No. 327,932, Oct. 24, 1994, abandoned.
[51] Int. Cl.$^6$ ..................................................... A61K 31/70
[52] U.S. Cl. ................................ 514/45; 514/42; 514/43; 514/46; 514/47; 514/48; 514/49; 514/50; 514/51; 536/4.1; 536/17.2; 536/17.3; 536/18.1; 536/18.4; 536/27.23; 536/27.6; 536/27.8; 536/27.81; 536/28.1; 536/28.53; 536/28.54
[58] Field of Search .................................. 514/25, 45, 46, 514/49, 50, 42, 47, 48, 51; 536/4.1, 17.2, 17.3, 18.1, 18.4, 27.23, 27.6, 27.8, 27.81, 28.1, 28.53, 28.54

[56] References Cited

U.S. PATENT DOCUMENTS

| | | | |
|---|---|---|---|
| 3,457,255 | 7/1969 | Jones et al. | 536/27.22 |
| 3,817,982 | 6/1974 | Verheyden et al. | 536/27.14 |
| 4,340,729 | 7/1982 | D'Souza et al. | 536/28.55 |
| 4,659,698 | 4/1987 | Imbach et al. | 514/49 |
| 4,880,782 | 11/1989 | Eckstein et al. | 514/45 |
| 4,918,056 | 4/1990 | Bobek et al. | 514/25 |

FOREIGN PATENT DOCUMENTS

| | | |
|---|---|---|
| A-24522/88 | 5/1989 | Australia . |
| 0 199 451 A2 | 10/1986 | European Pat. Off. . |
| 0 206 497 A2 | 12/1986 | European Pat. Off. . |
| 0 261 595 A2 | 3/1988 | European Pat. Off. . |
| 0 285 884 A2 | 10/1988 | European Pat. Off. . |
| 296 281 A5 | 11/1991 | German Dem. Rep. . |
| 1 620 185 | 2/1970 | Germany . |
| 1 378 408 | 12/1974 | United Kingdom . |
| WO88/00050 | 1/1988 | WIPO . |
| WO88/04662 | 6/1988 | WIPO . |
| WO90/01036 | 2/1990 | WIPO . |
| WO90/08147 | 7/1990 | WIPO . |
| WO92/06102 | 1/1992 | WIPO . |
| WO92/08727 | 5/1992 | WIPO . |
| WO93/03733 | 3/1993 | WIPO . |

OTHER PUBLICATIONS

L.M. Lerner et al. (1987) Journal of Medicinal Chemistry 30(8):1521–1525.
L. Novotny et al. (1994) Collection of Czechoslovak Chemical Communications 59(7)1691–1698.
K.A. Watanabe et al. (1974) Journal of Organic Chemistry 39(17)2482–2486.
H. Aoyama, Bull. Chem. Soc. Jpn., 60:2073–2077 (1987).
M. Asai, et al., Chem. Pharm. Bull., 15(12), 1863–1870 (1967).
U. Asseline, et al., Nucleic Acids Research, vol. 19, No. 15, 4067–4074 (1991).

M.V. Baud, et al., Tetrahedon Letters, vol. 31, 4437–4440 (1990).
A. Bloch, et al., J. Med. Chem., vol. 10, No. 5, 908–912 (1967).
G. Etzold, et al., Chem. Ber., 101:226–234 (1968).
V. Fucik, et al., Nucleic Acids Research, vol. 1, No. 4,639–644, Apr. 1974.
S. Fujimori, et al., Nucleosides & Nucleotides, 11(2–4), 341–349 (1992).
C. Genu–Dellac, et al., Nucleocides & Nucleotides, 10(6), 1345–1376 (1991).
C. Genu–Dellac, et al., Antiviral Chem. & Chemother. 2(2), 83–92 (1991).
C. Genu–Dellac, et al., Tet. Letters, vol. 32, No. 1, 79–82 (1991).
G. Gosselin, et al., Antmicrob. Agents Chemother., vol. 38, No. 6, 1292–1297, Jun. 1994.
J.G. Gu, et al., J. Neurochemistry, vol. 56, 548–552 (1991).
A. Holy, Nucleic Acid Chemistry, Part 1, 347–353, Eds. L.B. Townsend and R.S. Tipson, Wiley & Sons, New York (1978).
A. Holy, et al., Biol. Chem. Hoppe–Seyler, 366:355–359, Apr. 1985.
A. Holy, Nucleic Acid Chemistry, vol. 2, 527–532 (1978).
A. Holy, et al., Coll. Czech. Chem. Commun., vol. 34 (1969).
M. Jurovcik, et al., Febs Letters, vol. 18, No. 2, 274–276 (1971).
A.M. Kritzyn, et al., Coll. Czech. Chem. Commun., vol. 40, 3211–3219 (1975).
P. Langen, et al., Progress in Antimicrobial and Anticancer Chemotherapy, Proceedings of the 6th International Congress of Chemotherapy, University Park Press, England, 1970, vol. II, 394–397.
K.F. Lau, et al., Cancer Chemotherapy Reports, Part II, vol. 3,95–109 (1972).
L.M. Lerner, Preparation of Nucleosides, vol. 34, No. 1, 101–103 (1969).
M. Miwa, et al., Chem. Pharm. Bull., 38(4), 998–1003 (1990).
D.H. Murray, et al., J. Phar. Sci., vol. 56, No. 7, 865–870 (1967).
N. Nagasawa, et al., J. Org. Chem., 32:251–252 (1967).
C. Perigaud, et al., Nucleosides & Nucleotides, 11(2–4), 903–945 (1992).
S. Savithiry, et al., Physiol. Plant., 84:460–466 (1992).
B. Schwarz, et al., Coll. Czech. Chem. Commun. 45:3217–3230 (1980).

(List continued on next page.)

*Primary Examiner*—James O. Wilson
*Attorney, Agent, or Firm*—Debra J. Glaister

[57] ABSTRACT

This invention relates to α and β-L-pyranosyl nucleosides of Formula (I), wherein the nucleoside substitution on the pyranosyl carbohydrate molecule comprises a substituted or unsubstituted purine (adenine or guanine) or pyrimidine (cytosine, uracil, thymine and hypoxanthine) base. Also provided are methods to make the α and β-L-pyranosyl nucleosides and methods of using such to treat cancer in a mammal.

11 Claims, No Drawings

OTHER PUBLICATIONS

B. Shimizu, et al., Chem. Pharm. Bull., 15(12):2011–2014 (1967).

B. Shimizu, et al., Nucleic Acid Chemisrty, vol. 2, 783–792 (1978).

S. Spadari, J. Med. Chem., 35:4214–4220 (1992).

R.A. Taube, et al., Biochimica et Biophysica Acta, 255:6–18 (1972).

I. Votruba, et al., Febs Letters, vol. 19, No. 2, 136–138 (1971).

M.A. Waqar, et al., J. Cell. Physiol., 121:402–408 (1984).

A.F. Wu, et al., Biochemistry, 63:1222–1226 (1969).

Arteaga et al., Cancer Research, vol. 47, pp. 6248–6253, (1987).

Scheithaver et al., Cancer Research, vol. 46, pp. 2703–2708, (1986).

Hanauske et al., Selective Cancer Therapeutics, vol. 5, No. 3, pp. 97–111, (1989).

L-PYRANOSYL NUCLEOSIDES

This is a Continuation of application Ser. No. 08/327,932 filed Oct. 24, 1994, now abandoned.

FIELD OF THE INVENTION

This invention relates to L-pyranosyl nucleosides, processes for their preparation, pharmaceutical compositions containing such and methods of using such compounds as anticancer, antiviral, antifungal, antiparasitic and/or antibacterial agents in mammals.

BACKGROUND OF THE INVENTION

Perigaud, C. et al., *Nucleosides and Nucleotides*, 11 (2–4), 903–945, (1992) provide a useful overview of the current state of the art relating to the use of nucleosides and/or nucleotides as chemotherapeutic agents (including use as anticancer, antiviral and antibacterial agents). As described in this review article, the term "nucleoside(s)" relates to naturally-occurring nucleosides which are distinguished depending on the base, for example, adenine and guanine (A and G, respectively) have a purine base, whereas cytosine, uracil, thymine and hypoxanthine (C, U, T, and H, respectively) have a pyrimidine base.

Nagasawa, N., et al., *J. Org. Chem.*, 32, 251–252, (1967) describe the production of certain D-ribopyranosyl nucleosides (particularly 9-(2'-Deoxy-β-D-ribopyranosyl) adenosine. Fucik, V., et al., *Nucleic Acids Research*, Vol. 1, No. 4, (1974), 639–644, describe structural effects of chemical modification upon the affinity of purine nucleosides to cytidine-transport system in *Bacillus subtilis* using a series of modified derivatives including certain ribopyranosyl nucleosides.

As is well known, sugars found in natural nucleic acids are D-ribose and D-deoxyribose in almost all cases. Much research has been done to investigate the chemical and biological activities of the D-isomers of ribonucleotides and ribonucleosides, however, far less work has been done with the L-isomers. This is primarily due to the fact that the synthesis of the L-isomers is much more difficult, often involving the optical resolution of the D, L-isomers of nucleosides with the aid of microorganisms and enzymes. (See generally, Asai, M., et al., *Chem. Pharm. Bull.*, 15(12), 1863–1870, (1967)). The known activity of D-nucleoside compounds, and the successful commercialization of many of such D-sugar nucleosides (see Perigaud, C., et al., supra, for a discussion of D-nucleoside analogs which have gained commercial acceptance) lead in part to the present work relating to the L-isomers of certain nucleoside analogs.

Perhaps the best known commercial nucleobase analog is 5-fluorouracil (5-FU) the structure of which is shown below:

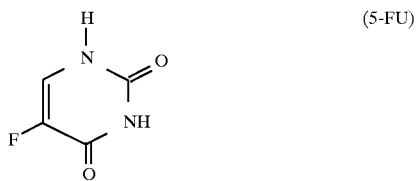

(5-FU)

5-FU is an antimetabolite compound commercially available from Roche and is one of the most commonly used drugs for treating certain types of cancer. The high acceptance of this drug is due in part to its extreme cytotoxic effects. However, this highly toxic compound has a narrow margin of safety and it has many side effects including, for example, GI side effects like nausea, vomiting and diarrhea, leukopenia, thrombocytopenia, alopecia, etc. Additionally, 5-FU is primarily used as an intravenous formulation. Therefore, there is a need for a nucleoside analog which is perhaps as cytotoxic as 5-FU or which is less cytotoxic but more specific than 5-FU, and which preferably can be administered orally.

5-FU is currently dosed at short intervals due to the damage it does to normal cells. The patient is taken off chemotherapy for a time to allow recovery from the cytotoxic effects of the treatment. It is contemplated that if a drug is developed that is less cytotoxic to healthy cells it would no longer be necessary to treat the patient in periodic intervals, which may be associated with the development of multiple drug resistance often exhibited in treated cancer cells. Specifically, as a tumor is being killed the cells that are most resistant to the drug die slower and, therefore, when the treatment is stopped (often because of the toxicity to normal cells), the more resistant tumor cells are left to multiply.

A significant commercial nucleoside analog is azidothymidine (AZT), commercially available as Retrovir from Burroughs Wellcome. AZT, a β-D-deoxy-ribofuranosyl derivative of the formula:

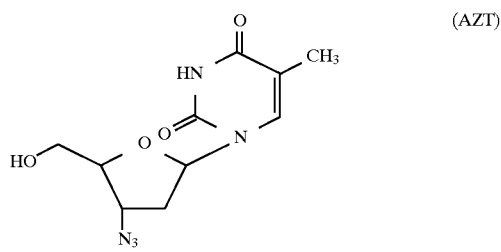

(AZT)

is useful as an antiviral agent, particularly against the virus responsible for the Acquired Immune Deficiency Syndrome (AIDS).

This compound, like 5-FU, is associated with a number of undesirable side effects including hematologic toxicity such as granulocytopenia and/or severe anemia.

Without intending to be limited, applicants believe that the L-nucleoside compounds, as claimed in the present invention, may be beneficial over compounds such as 5-FU and AZT since it is believed that L-nucleosides (as claimed) exhibit selective permeability to compromised cells. By compromised cells we mean cells such as cancer cells or other infected cells whether the infection is bacterial, fungal, viral or parasitic. It is believed that the L-nucleosides of the present invention may be transported into or permeate these compromised cells, whereas in normal cells the L-nucleosides would not permeate. (See, for example, Lin, T. S., et al., Abstract entitled "Synthesis and Biological Evaluation of 2', 3'-Dideoxy-L-Pyrimidine Nucleosides as Potential Antiviral Agents against HIV and HBV", published *J. Med. Chem.*, (1994), 37, 798–803; and Spadari, S., et al., *J. Med. Chem.*, (1992), 35 4214–4220.) Therefore, to the extent these L-nucleosides are selective for compromised cells, they are less harmful to normal cells than compounds like 5-FU.

In addition to this concept of selective permeability, in viral-infected cells where therapeutic compounds often have an inhibitory mechanism related to the RNA of the cell, it is contemplated that the enzymes of such viral-infected cells may be less specific than in a normal cell and, therefore, if you can permeate the cell with an L-nucleoside, a more primitive enzyme (such as an organic phosphorylases, kinase or thymidylate synthase) may recognize the compound in such a way as to cause inhibition.

The present invention, therefore, relates to a novel group of such L-pyranosyl nucleosides which have interesting activity as anticancer, antiviral, antiparasitic, antifungal and/or antimicrobial agents. These compounds are generally water soluble, which suggests that oral deliver may be achieved. This would be specifically advantageous versus anticancer compounds such as 5-FU. And the activity of these compounds may be more selective for compromised cells as compared to normal cells, suggesting that compounds of this invention will cause fewer side effects than similar compounds such as 5-FU.

DETAILED DESCRIPTION OF THE INVENTION

There is provided by this invention pyranosyl nucleoside compounds having the formula (I):

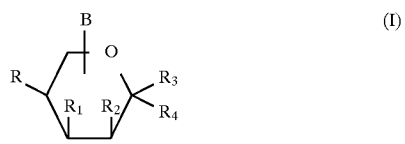

or a pharmaceutically acceptable salt thereof wherein:

B is a naturally-occurring nucleobase (A,G,C,U,T or hypoxanthine) or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, a substituted amino group, an aryl, aralkyl, aryloxy, aralkoxy, arylthio, aralkylthio, a heterocyclic ring and an amino group, provided that when the base is a pyrimidine, the atom at position 4 in the base can be sulfur and that when the base is a purine, the atom at position 6 in the base may be sulfur;

R is $OR_5$ (wherein $R_5$ is H, $COR_6$, or $P(O)_n R_7 R_8$ (wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3));

$R_1$ and $R_2$ are independently H, mono- or di-halogen, $OR_9$, or B (wherein $R_9$ is H, $COR_{10}$, $P(O)_m R_{11} R_{12}$ (wherein $R_{10}$ is substituted or unsubstituted alkyl of 1–5 carbon atoms or a substituted or unsubstituted aromatic ring structure and $R_{11}$ and $R_{12}$ are each H or alkyl of 1–5 carbon atoms and m is 2 or 3)); and $R_3$ and $R_4$ are independently B, H or $OR_{13}$ (wherein $R_{13}$ is H, $COR_{14}$, $P(O)_p R_{15} R_{16}$ (wherein $R_{14}$ is substituted or unsubstituted alkyl of 1–5 carbon atoms or a substituted or unsubstituted aromatic ring structure and $R_{15}$ and $R_{16}$ each are H or alkyl of 1–5 carbon atoms and p is 2 or 3)), provided that only one of $R_1$–$R_4$ can be B; and further provided that when R and $R_1$ are each OH, $R_2$ is H, and $R_3$ is B, then B can not be thymine; and when R and $R_1$ are each OH, $R_2$ is H, and $R_4$ is B, then B cannot be thymine.

Preferred compounds of the present invention include those compounds of formula (I) wherein:

one of $R_3$ or $R_4$ is B and the other is H, such that when $R_3$ is B the series is α and when $R_4$ is B the series is β;

B is C, T, U, G, A or 5-fluorouracil; and

R–$R_2$ are each OH.

Specifically preferred compounds of the present invention are the following:

β-L-ribopyranosylcytosine; β-L-ribopyranosylguanine; β-L-ribopyranosyladenosine; β-L-ribopyranosyluracil; β-L-ribopyranosyl-5-fluorouracil; and α-L-ribopyranosyl-5-fluorouracil and pharmaceutically acceptable salts thereof.

Also provided by this invention are processes for the preparation of the compounds of formula (I), pharmaceutical compositions containing the compounds of formula (I), and methods of using the compounds of formula (I) for the treatment of cancer in a mammal (and particularly a solid tumor in a mammal), as well as methods of using the compounds of formula (I) as antiviral, antifungal, antiparasitic and/or antibacterial agents in a mammal.

Synthesis

The present invention describes a series of L-pyranosyl nucleosides useful for treating various diseases (including cancer). Compounds of this invention may be orally active based on their water solubility.

The compounds of this invention, wherein the nucleoside has a pyrimidine base (U,T,C or substituted pyrimidine base) which is linked to the pyranosyl sugar via β linkage (B is $R_4$ in a compound of Formula (I)), can be made by the general Scheme A.

SCHEME A

General procedure to make β-L-Ribopyranosyl pyrimidines:

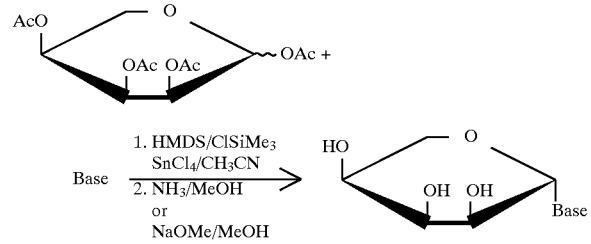

To a mixture of tetraacetyl-L-ribopyranoside (1 mol) and pyrimidine base (1 mol) in anhydrous MeCN are successively added HMDS (1 mol), ClSiMe₃ (0.8 mol) and SnCl₄ (1.2 mol). The resulting clear solution is refluxed for 1 hour when TLC indicates completion of the reaction. The solvent is evaporated and the residue dissolved in EtOAc, washed with NaHCO₃ and H₂O. The EtOAc layer is dried, filtered and evaporated to give the crude product, which is either crystallized or purified on a silica column to obtain the pure 2,3,5-tri-O-acetyl-L-ribopyranosyl pyrimidine compounds. These compounds are either stirred with NH₃/MeOH or NaOMe in MeOH to give the pure β-L-ribopyranosyl pyrimidines after purification and crystallization.

A more detailed scheme for the synthesis of specific β-linked pyrimidine compounds is provided as Scheme A-1.

SCHEME A-1

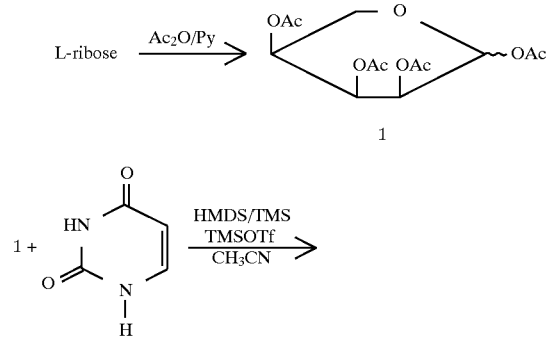

-continued
SCHEME A-1

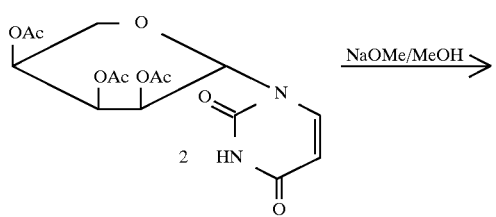
2

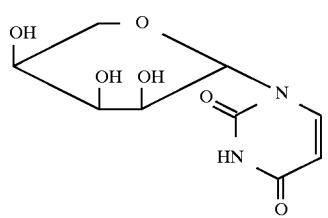
3

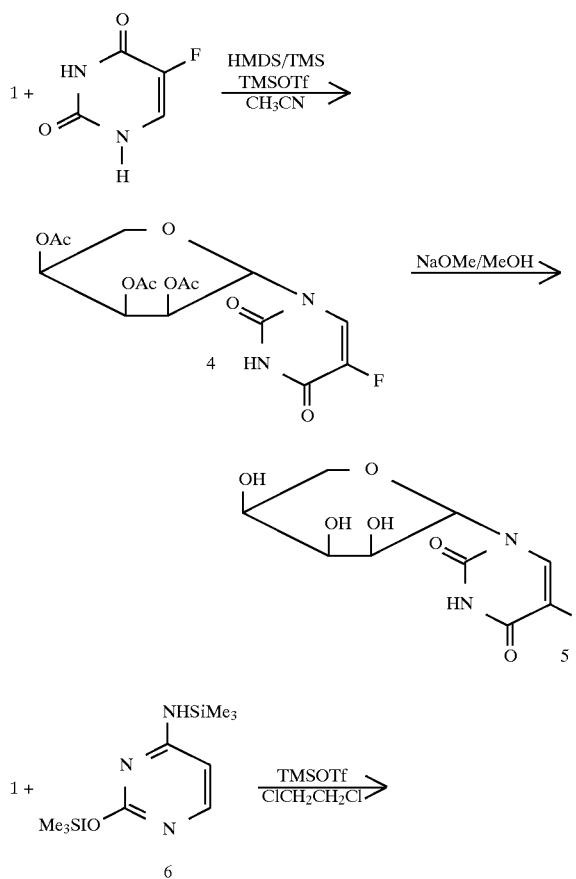

-continued
SCHEME A-1

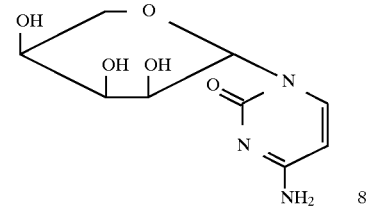
8

The compounds of this invention wherein the nucleoside has a purine base (A or G or substituted purine base) which is linked to the pyranosyl sugar via β link (B is $R_4$ in a compound of Formula (I)) can be made by the general scheme B below.

SCHEME B

General procedure to make β-L-ribopyranosyl purines:

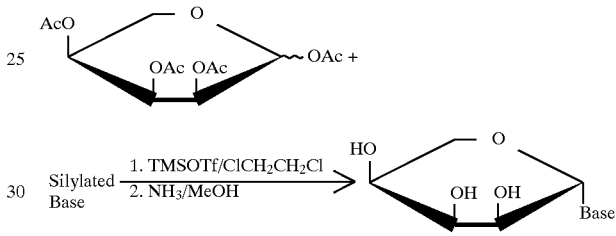

A mixture of purine base (2 mol) and $(NH_4)_2SO_4$ (catalytic amount) in HMDS is refluxed until the solution becomes clear. The resulting clear solution is concentrated to yield silylated base to which anhydrous dichloroethane is added, and the solution is cooled to 0° C. Under nitrogen atmosphere a solution of tetraacetyl-L-ribopyranoside in dichloroethane (1 mol) and TMSOTf (2.1 mol) are added to the above solution and stirred at room temperature for 16 hours. The reaction is quenched with saturated $NaHCO_3$ solution and the solvent is evaporated. The residue is dissolved in EtOAc, washed with water and brine. After drying and evaporating the solvent, the residue obtained is purified on a silica gel column to give pure 2,3,5-tri-O-benzyl-β-L-ribopyranosyl purines and which, after stirring with $NH_3$/MeOH and usual purification, give pure β-L-ribopyranosyl purines.

A more detailed schematic for the synthesis of specific β-linked purine compounds is provided as Scheme B-1.

SCHEME B-1

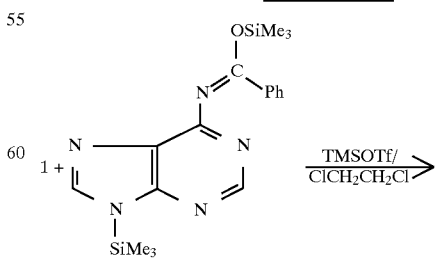
9

-continued
SCHEME B-1

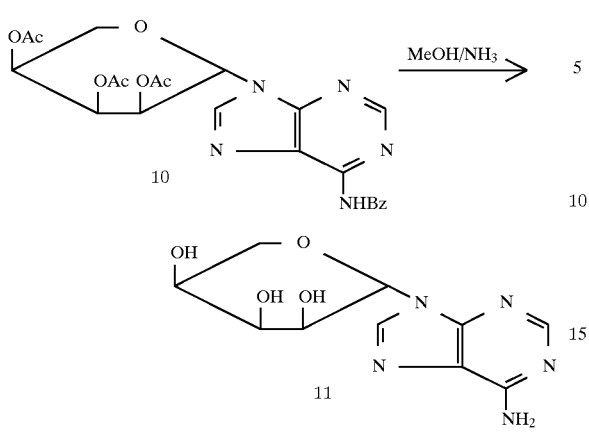

The compounds of this invention wherein the nucleoside has a pyrimidine base (U,T,C,H or substituted pyrimidine base) which is linked to the pyranosyl sugar via α linkage (B is R₃ in a compound of Formula (I)) can be made by the general scheme C below.

SCHEME C

General procedure to make α-L-Ribopyranosyl pyrimidines:

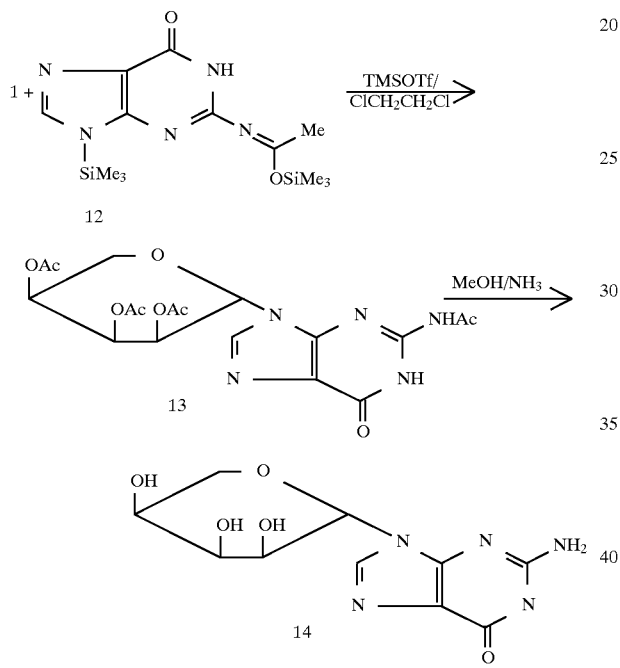

A mixture of pyrimidine base (2 mol) in HMDS and ammonium sulfate (catalytic amount) is refluxed until the solution becomes clear.

The resulting clear solution is concentrated in vacuo to yield silylated base. To this silylated base in anhydrous CH₂Cl₂ under nitrogen atmosphere, 1-thio-2,3,5-tri-O-benzyl-L-ribopyranoside (2 mol), 4 Å molecular sieves and NBS (1.1 mol) are added. The reaction mixture is stirred at room temperature overnight and quenched with addition of Na₂S₂O₃ solution. The organic layer is washed with water, brine and dried over Na₂SO₄. Evaporation of the solvent gave the crude product which is purified on a silica gel column to obtain pure 2,3,5-tri-O-benzyl-α-L-ribopyranosyl pyrimidine compounds. These compounds are subjected to H₂/Pd/C reduction followed by purification and crystallization to give pure α-L-ribopyranosyl pyrimidines.

A more detailed schematic for the synthesis of specific α-linked pyrimidine compounds is provided in Scheme C-1.

SCHEME C-1

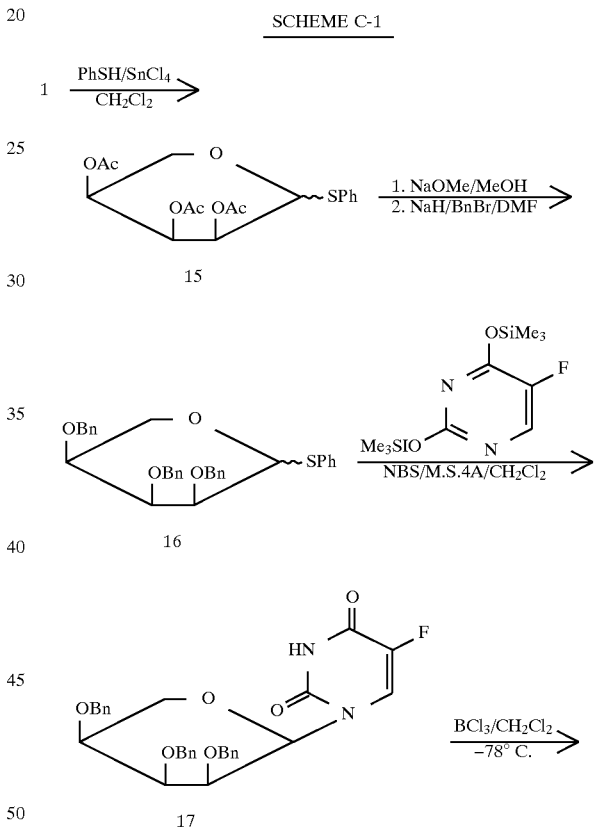

Compounds of this invention wherein the nucleoside has a purine base which is linked to the pyranosyl via α linkage can be made by the general Scheme D below.

SCHEME D

General procedure to make α-L-ribopyranosyl purines:

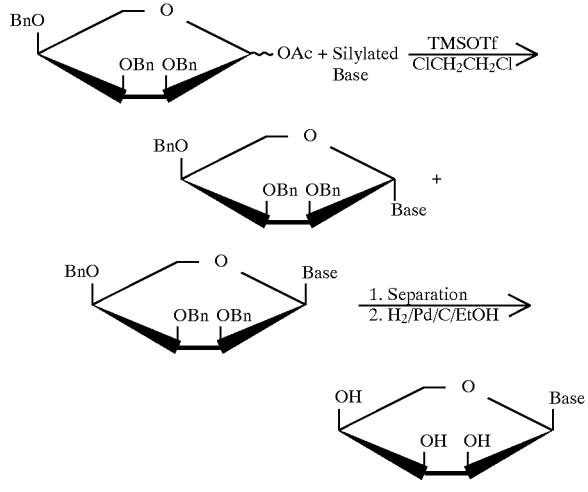

A mixture of purine base (2 mol) and (NH$_4$)$_2$SO$_4$ (catalytic amount) in HMDS is refluxed until the solution becomes clear. The resulting clear solution is concentrated to yield silylated base to which anhydrous dichloroethane is added and the solution is cooled to 0° C. Under nitrogen atmosphere a solution of 1-O-acetyl-2,3,5-tri-O-benzyl-L-ribopyranose and TMSOTf (2.1 mol) are added to the above solution and stirred at room temperature for 16 hours. The reaction is quenched with saturated NaHCO$_3$ solution and the solvent is evaporated. The residue is dissolved in EtOAc, washed with water and brine. After drying and evaporating the solvent, the residue obtained is separated on a silica gel column to give pure α and β-2,3,5-tri-O-benzyl-L-ribopyranosyl purines and which after reduction with hydrogen in presence of Pd/C catalyst (H$_2$/Pd/C) and usual purification give pure α-L-ribopyranosyl purines.

A more detailed schematic for α-linked purine compounds within the scope of the present invention is provided below as Scheme D-1.

SCHEME D-1

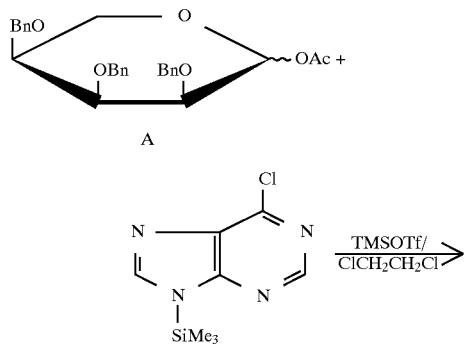

SCHEME D-1 -continued

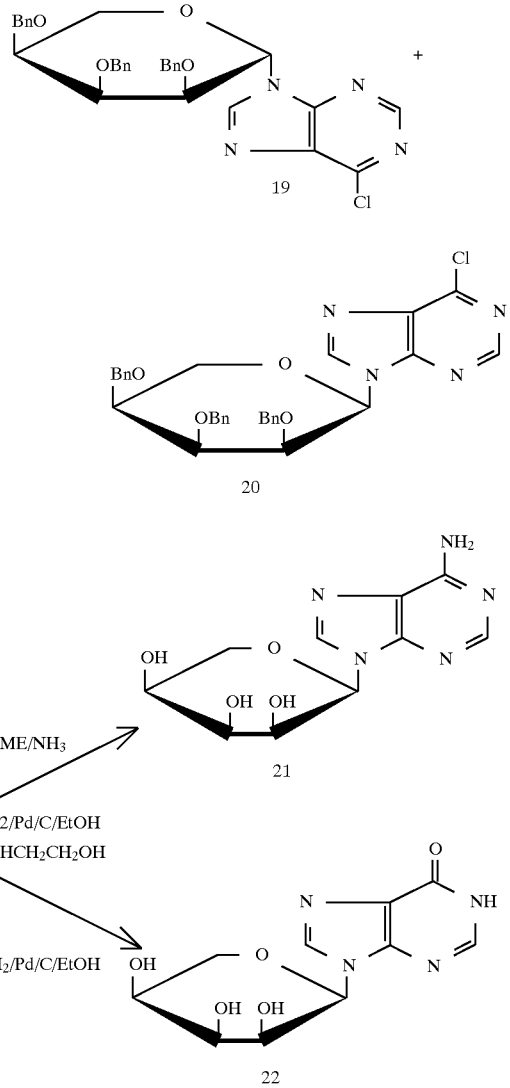

21 = α-L-Ribopyranosyladenine
22 = α-L-Ribopyranosylhypoxanthine
25 = α-L-Ribopyranosylguanine

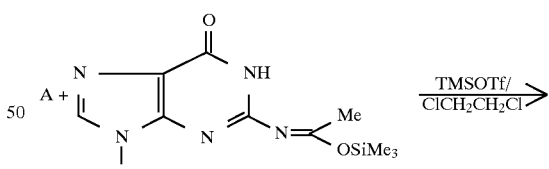

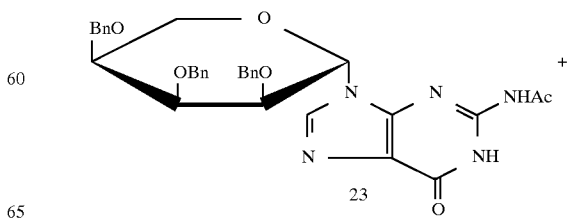

-continued
SCHEME D-1

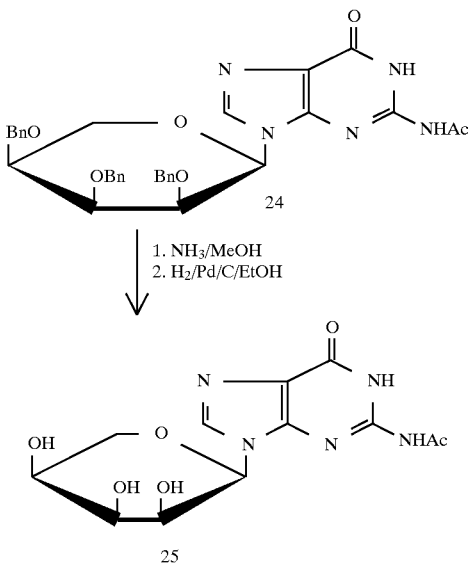

In addition to the teachings provided herein, the skilled artisan will readily understand how to make compounds within the scope of the present invention by applying well known techniques such as those described in *Nucleic Acid Chemistry, Improved and New Synthetic Procedures, Methods and Techniques*, Edited by Leroy B. Townsend and R. Stuart Tipson, John Wiley & Sons, New York (1978); and *Chemistry of Nucleosides and Nucleotides*, Edited by Leroy B. Townsend, N.Y., Plenum Press (1988–1991). Suitable methods for making various substitutions on purine nucleosides are provided in WO90/08147. Suitable methods for making substitutions on pyrimidine nucleosides are provided in WO88/04662. The disclosure of both such applications and their US equivalent applications/patents being readily available to those skilled in the art and incorporated herein. Suitable methods for making substitutions within the sugar moiety of the presently claimed compounds are known to those skilled in the art and are described in various publications including: U.S. Pat. No. 4,880,782; WO88/00050; EPO 199451 A2; U.S. Pat. No. 3,817,982; Lange, P., et al., *Progress in Antimicrobial and Anticancer Chemotherapy*, Proceedings of the 6th International Congress of Chemotherapy, Univ. Park Press, England, 1970, Vol. II, p. 394–397; and Townsend, et al., supra, all of which are incorporated herein by reference.

This invention can be further understood by referring to the following Examples and Tables below:

EXPERIMENTAL

Example 1

β-L-ribopyranosyluracil and β-L-ribopyranosyl-5-fluorouracil

Part A

Synthesis of 1,2,3,4-tetraacetyl-L-ribopyranoside (1)

The mixture of L-ribose (commercially available from Sigma Chemical Co.) (6.0 g), acetic anhydride (80 ml) and pyridine (12 ml) was heated to 100° C. with stirring until the L-ribose dissolved. After cooling acetic anhydride was evaporated in vacuo. The residue was dissolved in 100 ml of dichloromethane and washed 3×50 ml of saturated $NaHCO_3$ solution and 50 ml satd. NaCl solution. Organic phase was dried over sodium sulfate and the solvent was evaporated on a rotovapor. Finally, the oily residue was kept overnight at high vacuum to give (1) as a white crystalline solid (12.3 g, 96.7%). TLC:$R_f$=0.63 in ethyl acetate-petroleum ether (7:3).

Part B

Synthesis of β-L-ribopyranosyluracil triacetate (2) and β-L-ribopyranosyl-5-fluorouracil triacetate (4)

To 1,2,3,4-tetraacetyl-L-ribopyranoside (1, 3.5 g, 11 mmol) and uracil (commercially available from Sigma Chemical Co.) (1.23 g, 11 mmol) or 5-fluorouracil (commercially available from Sigma Chemical Co.) (1.43 g, 11 mmol) in 80 ml of dry acetonitrile were added hexamethyldisilazane (2.3 ml, 8.8 mmol), trimethyl-chlorosilane (1.1 ml, 8.8 mmol) and trimethylsilyl triflate (3.6 ml, 18 mmol). The reaction mixture was stirred for about 16 h at room temperature, then refluxed for 1.5 h to complete the reaction. After cooling the reaction mixture was diluted with 100 ml of dichloromethane and washed with 3×50 ml of satd. sodium hydrocarbonate solution. The combined aqueous phases were re-extracted with 50 ml of dichloromethane. The combined organic phases were washed with 50 ml satd. NaCl solution. The organic phase was dried over sodium sulfate and the solvent was evaporated on a rotovapor to give pale yellow crystals. Yields were 3.1 g (76%) for β-L-ribopyranosyluracil triacetate (2) and 2.9 g (69.9%) for β-L-ribopyranosyl-5-fluorouracil (4) derivate. Crude products were purified by flash chromatography on a silica gel column (150 g) using ethylacetate-petroleum ether (7:3) eluent. Yields: 2.0 g (52%) and 2.5 g(56%), respectively. TLC:$R_f$=0.18 in ethylacetate-petroleum ether (7:3) for both compounds..

Part C

Synthesis of β-L-ribopyranosyluracil (3) and β-L-ribopyranosyl-5-fluorouracil (5)

Triacetates from Part B were deprotected by treating with 2.0M methanolic ammonia (80 ml for 10 mmol nucleoside) for 24 h at room temperature. (The methanolic ammonia was evaporated in vacuum and the residue was purified by flash chromatography on silica gel (150 g) with chloroform-methanol-water (65:35:4) eluent to give 1.4 g (36% overall yield) L-ribopyranosyluracil (3), and 1.8 g (40% overall yield) L-ribopyranosyl-5-fluorouracil (5) white crystals. TLC:$R_f$=0.4 for both compounds in chloroform-methanol-water (65:35:4) solvent.

$^1$H-NMR For (3) (DMSO-d6) δ

3.52–3.75 (m,4H, H-3', 4', & 5') 3.95 (m,1H, H2') 4.84 (d, 1H, OH)

5.06 (d, 1H, OH) 5.10 (d,1H, OH) 5.58 (d, 1H, H-2') 5.60 (d,1H, H-1')

7.65 (d, 1H, H-6)

$^1$H-NMR For (5) (DMSO-d6) δ

3.45–3.80 (m, 4H, H-3', 4'& 5') 4.0 (m,1H, H2') 4.8–5.4(br s, 3H, 2', 3' & 5'OH)

5.60 (d,1H, H-1') 8.10 (d,1H, H-6)

Example 2

β-L-Ribopyranosylcytosine

Part A

Synthesis of 2-trimethylsilyloxy-4-trimethylsilyl amino pyrimidine (6)

The mixture of cytosine (1.7 g, 15.3 mmol), hexamethyldisilazane (HMDS) (15 ml), trimethyl-chlorosilane (TCS) (0.1 ml) and pyridine (10 ml) was refluxed at 130° C. bath temperature until the complete dissolving of cytosine (about 1.5 h). The excess HMDS and pyridine was removed by co-distillation with 2×50 ml of dry toluene. White solid was dried in high vacuum. Yield: 3.8 g (6) (97.3%). TLC:$R_f$=0.42 ethyl acetate-petroleum ether (7:3).

Part B

Synthesis of β-L-ribopyranosylcytosine triacetate (7)

To 1,2,3,4-tetraacetyl-L-ribopyranoside (1, 4.1 g, 12.9 mmol) and silylated cytosine (6) (3.3 g, 12.9 mmol) dissolved in 80 ml of dry acetonitrile was slowly added trimethylsilyltriflate (2.8 ml, 14 mmol). The mixture was stirred 72 h at room temperature. The reaction was completed by refluxing the mixture for 1 h. The dark brown solution was diluted with 150 ml of dichloromethane and washed 3×50 ml of satd. sodium bicarbonate solution. The aqueous layer was re-extracted with 50 ml of dichloromethane. The combined organic phases were dried over sodium sulfate and the solvent evaporated on a rotovapor. The residue was dried in vacuo to give 3.8 g (80%) brownish foam. The product was purified by flash chromatography on a silica gel column (150 g) with ethyl acetate-methanol (9:1) eluent. Yield: 1.5 g (7) (31.5%) orange crystalline material. TLC:$R_f$=0.51 ethyl acetate-methanol (9:1).

Part C

Synthesis of β-L-ribopyranosylcytosine (8)

β-L-ribopyranosylcytosine triacetate (7) was deprotected by treating with 2.0M methanolic ammonia (80 ml for 10 mmol nucleoside) for 24 h at room temperature. The methanolic ammonia was evaporated in vacuo and the residue was purified by flash chromatography on silica gel (150 g) with chloroform-methanol-water (65:35:4) eluent to give (8) 0.8 g (17% overall yield) of white needles. TLC:$R_f$=0.17 in chloroform-methanol-water (65:35:4) as a mobile phase.

'H-NMR For (8) (DMSO-d6) δ
3.42–3.65 (m, 4H, H-3', 4' & 5') 3.95 (m,1H, H-2') 4.79 (d, 1H, OH)
4.84 (d, 1H, OH) 5.01 (d, 1H, OH) 5.67 (d, 1H, H-5') 5.71 (d, 1H, H-5)
7.13 (br d, 1H, NH$_2$) 7.55 (d,1H, H-6)

Example 3

β-L-ribopyranosyladenosine (11)

N$^6$-benzoyl-adenine (2.392 g, 10 mmol) was silylated by heating at reflux temperature for 7 hrs with hexamethyldisilazane (35 ml), trimethyl-chlorosilane (0.5 ml) in the presence of dry pyridine (10 ml). The solvents were removed in vacuo. The traces of silylating agents were removed by co-distillation with dry toluene (2×20 ml) and the resulting off-white solid (9) was used for nucleoside synthesis.

Silylated N$^6$-benzoyladenine (9) (10 mmol) was reacted with 1,2,3,4-tetraacetyl-L-ribopyranoside (1, 3.18 g, 10 mmol) in dry acetonitrile (50 ml) using trimethylsilyl triflate catalyst (2.2 ml, 11 mmol). The clear solution after the addition of catalyst was refluxed for 14 h. TLC indicated no starting sugar and silylated benzoyladenine. The reaction mixture was diluted with 100 ml of dichloromethane and washed with 3×50 ml of cold satd. sodium bicarbonate solution. The organic phase was dried over sodium sulfate and evaporated to give brown glassy product. Purification by flash chromatography (chloroform-methanol 95:5) yielded 3.5 g of greenish solid. After dissolving in methanol (50 ml) the product was treated with active carbon (1.2 g). Filtration of this solution followed evaporation on a rotovapor afforded 2.5 g (10) of pale yellow amorphous crystalline material. After deprotection with 100 ml of methanolic ammonia yielded (11) 1.0 g (39%) as off-white crystals. $R_f$=0.36 in n-butanol-acetic acid-water (12:3:5).

'H-NMR For (11) (DMSO-d6) δ
3.55–3.78 (m, 3H, H-4' & 5') 4.04 (m, 1H, H-3') 4.23 (t, 1H, H-2')
4.91 (d, 1H, OH) 5.08 (d, 1H, OH) 5.15 (d, 1H, OH) 5.63 (d, 1H, H-1')
7.25 (s, 2H, NH$_2$) 8.14 & 8.30 (s, 2H, H-2 & 8)

Example 4

β-L-ribopyranosylguanine (14)

Part A

N$^2$-acetyl-guanine (2.13 g, 11 mmol) was silylated by heating at reflux temperature for 7 h with hexamethyldisilazane (35 ml), trimethyl-chlorosilane (0.5 ml) in the presence of dry pyridine (10 ml). The solvents were removed in vacuo. The traces of silylating agents were removed by co-distillation with dry toluene (2×20 ml). The resulting off-white solid (12) was used for nucleoside synthesis.

Part B

Silylated N$^2$-acetyl-guanine (12) (10 mmol) was reacted with 1,2,3,4-tetraacetyl-L-ribopyranoside (1, 3.5 g, 11 mmol) in dry acetonitrile (50 ml) using trimethylsilyl triflate catalyst (2.42 ml, 12.1 mmol). The clear solution after the addition of catalyst was refluxed for 1.5 h and stirred at room temperature for 12 h. TLC showed no parent base of silylated base or sugar. The reaction mixture was diluted with 100 ml of dichloromethane and washed with 3×50 ml of cold satd. sodium bicarbonate solution. Organic phase was dried over sodium sulfate and evaporated to give 3.4 g yellow amorphous crystalline material. Purification by flash chromatography (chloroform-methanol 95:5) yielded 1.9 g (13) of off-white crystals. After deprotection with 100 ml of methanolic ammonia yielded (14) 1.0 g (45%) as off-white crystals. $R_f$=0.22 in n-butanol-acetic acid-water (12:3:5).

'H-NMR For (14) (DMSO-d6) δ
3.50–3.65 (m, 3H, H-4' & 5') 3.95–4.15 (m, 2H, H-2' & 3')
5.0 (br s, 3H, 2', 3' & 5'-OH) 5.50 (d, 1H, H-1') 6.60 (br s, 2H, NH$_2$) 7.83 (s, 1H, H-8)

Example 5

α-L-ribopyranosyl-5-fluorouracil (18)

Part A 1,2,3,4-Tetraacetyl-L-ribopyranoside (1)

To a solution of L-ribose (2.15 g, 14.32 mmol) in pyridine (10 ml), acetic anhydride (10 ml) was added and the reaction mixture was stirred at room temperature overnight. Solvents were evaporated and the residue was dissolved in EtOAc, washed with water, CuSO$_4$ solution, NaHCO$_3$ solution and brine. After drying and evaporating the solvent, an oil was obtained and it was used without further purification in the next step.

Part B

1-Thio-2,3,4-tri-O-acetyl-L-ribopyranoside (15)

To a solution of (1) (4.54 g, 14.28 mmol), in CH$_2$Cl$_2$ (80 ml), thiophenol (1.6 ml, 15.71 mmol) was added and stirred at room temperature for 15 min. Then the reaction mixture was cooled in an ice bath and SnCl$_4$ (1 ml, 8.56 mmol) was added dropwise and stirred at room temperature overnight. The reaction mixture was washed with 2N HCl (2×100 ml), water (150 ml), NaHCO$_3$ solution (100 ml) and then with brine. After drying over Na$_2$SO$_4$, the solvent was evaporated and the residue was purified on a silica gel column using 20–30% EtOAc/petroleum ether as solvent to give pure compound 15 (2.61 g, 49.7%) as an oil.

Part C

1-Thio-2,3,4-tri-O-benzyl-L-ribopyranoside (16)

To a solution of (15) (2.61 g, 7.08 mmol) in MeOH (50 ml), NaOMe (0.3 ml, 1.4 mmol) was added and stirred for 18 h. The reaction mixture was neutralized by Dowex 50 ion exchange resin, filtered and evaporated. To this residue, DMF (50 ml) was added and cooled in an ice bath. To this cooled solution NaH (2.67 g, 66.85 mmol) was added in portion and stirred for 15 min. Benzyl bromide (8 ml, 6.85 mmol) was added dropwise and stirred at 0° C. for 2–3 h. The reaction was quenched with MeOH and water after diluting with EtOAc. EtOAc layer was washed with water (2×100 ml) and brine. After drying and evaporation of the solvent, the crude product obtained was purified on a silica gel column using 5–10% EtOAc/petroleum ether as solvent to yield pure (16)(3.29 g, 93.5%) as an oil.

Part D 1-(2,3,4-Tri-O-benzyl-α-L-ribopyranosyl)-5-fluorouracil (17)

A mixture of 5-fluorouracil (1.62 g, 12.48 mmol) in hexamethyldisilazane (30 ml) and ammonium sulfate (catalytic amount) was refluxed for 4 h. The resulting clear solution was concentrated in vacuo to yield silylated 5-fluorouracil as colorless oil. To a solution of silylated 5-fluorouracil in $CH_2Cl_2$ (20 ml) under nitrogen atmosphere were added NBS (1.22 g, 6.86 mmol), 4 Å molecular sieves (2.4 g) and compound (16) (3.2 g, 6.24 mmol) in $CH_2Cl_2$ (20 ml). The reaction mixture was stirred at room temperature overnight and quenched with the addition of $Na_2S_2O_3$ solution. The organic layer was washed with water and brine and then dried over $Na_2SO_4$. Evaporation of the solvent gave the crude product and it was purified on a silica gel column using 50% EtOAc/petroleum ether as solvent to give the pure α isomer (17) (2.42 g, 73%) as white solid.

Part E

α-L-ribopyranosyl-5-fluorouracil (18)

To a solution of 17 (from Part D) (2.42 g, 4.54 mmol) in $CH_2Cl_2$ (100 ml), at −78° C. under nitrogen atmosphere, 1M solution of $BCl_3$ (50 ml, 49.94 mmol) was added dropwise. The reaction mixture was stirred at −78° C. for 4 h and 1:1 mixture of $CH_2Cl_2$/MeOH (100 ml) was added and the reaction mixture was brought to room temperature and the solvents were evaporated to dryness. The residue was coevaporated with MeOH (50 ml) 5 times. The residue obtained was dissolved in water and washed with $CHCl_3$ (50×2) and $CCl_4$ (50 ml). The water layer was evaporated to give a white solid and which was crystallized from EtOH/ether to give the pure 18 (0.94 g, 79.4%) as white crystals: mp 231° C. dec.

$^1$H-NMR For (18) (DMSO-d6) δ

3.62–3.80 (m, 3H, H-3', 4' & 5') 3.95 (d, 1H, H-2') 5.0–5.2 (2 br s, 2H, OH)

5.30 (d, 1H, OH) 5.50 (s,1H, H-1') 7.95 (d, 1H, H-6) 11.90 (brd, 1H, NH)

Utility

In vitro activity against certain human tumor cell lines. CELL LINES: Eight different established human cell lines (CALU (lung), COLO320 (colon), H578St (breast), HT-29 (colon), MCF-7 (breast), OM-1 (colon), SKLU (lung), and SKMES (lung) and two control cell lines (bone marrow cell lines and/or fibroblasts) were utilized. All cell lines were obtained from the Tumor Cloning Laboratory, Institute for Drug Development, Cancer Therapy and Research Center, San Antonio, Tex. All cell lines grew as monolayers in the appropriate culture medium supplemented with heat-inactivated calf serum. All reagents were obtained from Grand Island Biological Co., Grand Island, N.Y.

IN VITRO EXPOSURE OF TUMOR CELLS TO COMPOUNDS: Stock solutions of intravenous (iv) formulations of certain of the compounds of the present invention (as shown in Table I below), as well as intravenous formulations of 5-FU (control) were used. The iv formulations of the compounds of the present invention were prepared with sterile buffered saline and stored at −70° C. until required for testing. The 5-FU control formulation was prepared as suggested in the commercial product literature.

Following trypsinization, tumor cells were suspended in tissue culture medium and exposed to the antitumor agents continuously at three different concentrations: 10, 1 and 0.1 μg/ml.

RADIOMETRIC MEASUREMENT OF GROWTH INHIBITION: Growth inhibition was assessed with the BACTEC System 460 (Johnston Laboratories, Towson, Md.) after addition of the antitumor agent to the cells in the respective growth medium containing $^{14}$C-glucose at a final concentration of 2 μCi/ml. (See generally, C. Arteaga, et al., *A Radiometric Method for Evaluation of Chemotherapy Sensitivity: Results of Screening a Panel of Human Breast Cancer Cell Lines*, Cancer Research, 47, 6248–6253, (1987).)

Two mls of the tumor cell suspension containing radioactive glucose were seeded into sterile, disposable 15 ml vials by injection through self-sealing rubber-aluminum caps. For each cell line, the optimal number of tumor cells needed per vial in order to show significantly measurable growth in this radiometric system varied. The seeded vials were then incubated at 37° C. Measurement of the release of $^{14}CO_2$ resulting from the metabolism of $^{14}$C-glucose were performed on days 6, 9, 12, and 15 in the BACTEC instrument. This instrument flushes the $^{14}CO_2$ containing air out of the vials into an ionization chamber that converts dpm to growth index values. Chemotherapy sensitivity was calculated by comparing the growth index values of drug-treated vials to that observed in control vials. Each data point represents triplicate values.

Results are shown in Table I below. All compounds were compared on an equimilimolar level.

TABLE I

| COMPOUND | % SURVIVAL BONE MARROW | % SURVIVAL TUMOR | IC 50 (μg/ml) | |
|---|---|---|---|---|
| 5-FU (control) 6 μg/ml | 38.6 | CALU | 9.9 | <0.6 |
| | | SKMES | 29.1 | <0.6 |
| | | SKLU | 24.7 | 1.05 |
| | | COLO320 | 1.0 | <0.6 |
| | | HT-29 | 5.7 | 0.61 |
| | | OM-1 | 20.1 | 1.47 |
| | | HS578T | 12.5 | <0.6 |
| | | MCF-7 | 4.2 | <0.6 |
| (8) 10 μg/ml | 93.1 | OM-1 | 78.9 | >10 |
| | | HS578T | 89.2 | >10 |
| | | MCF-7 | 72.2 | >10 |
| (14) 10 μg/ml | 105.9 | HT-29 | 94.8 | >10 |
| (11) 10 μg/ml | 94.1 | OM-1 | 41.6 | 8.3 |
| | | HS578T | 43.6 | 7.8 |
| (3) 10 μg/ml | 96.0 | HS578T | 86.7 | >10 |
| (5) 10 μg/ml | 115.8 | SKMES | 68.2 | >10 |
| | | SKLU | 90.1 | >10 |
| | | MCF-7 | 76.2 | >10 |
| (18) 10 μg/ml | 165.7 | SKLU | 78.4 | 57.1 |
| | | HT-29 | 83.1 | 119 |
| | | OM-1 | 82.5 | 65.1 |
| | | HS578T | 83.6 | 50.8 |

The data presented in Table I are compared to results achieved with 5-FU as the control. All compounds were dosed on an equimilimolar basis. Inhibitory concentration (IC 50) is defined as the concentration required to kill 50% of the untreated cancer cells. Although the IC 50 of certain of the compounds listed in Table I may be higher than that for 5-FU (the control), the compounds of the present invention are generally less toxic to normal cells such as bone marrow or fibroblasts. This implies that the compounds of the present invention may have advantages over known cancer therapies as the claimed compounds may be less toxic and/or more selective for the tumor cells, thereby causing less serious side effects. Additionally, because of their lower toxicity to normal cells, it is anticipated that the present compounds may be dosed at a higher rate to selectively increase toxicity to the cancer cells. In this regard, a therapeutic ratio for a given compound is typically determined by the following calculation.

$$\frac{\% \text{ survival bone marrow}}{\% \text{ survival tumor}}$$

A therapeutic ratio of <80% is considered active.

In Vivo Evaluation

Representative compounds of the present invention have been and/or are being tested in a variety of preclinical tests of anti-cancer activity which are indicative of clinical utility. For example, certain compounds were tested in vivo against human tumors xenografted into nude mice, specifically B16, MX-1 and P388 Leukemia tumor lines were used.

B16 Melanoma

B6D2F1 mice receive i.p. inocula of B16 murine melanoma brei prepared from B16 tumors growing s.c. in mice (day 0). On day 1, tumored mice are treated with drugs or vehicle control; the drugs, route of drug administration, and schedule are selected as appropriate for the study in question. If dosing information for agents is not available, the maximum tolerated dose (MTD) is determined in initial dose finding experiments in non-tumored mice. In a typical experiment, drugs are given at their MTD and ½ MTD doses i.p. on a daily×5 schedule.

The mean survival times of all groups are calculated, and results are expressed as mean survival of treated mice/mean survival of control mice (T/C)×100. A T/C value of 150 means that the treated group lived 50% longer than the control group; this is sometimes referred to as the increase in life span, or ILS value.

Mice that survive for 60 days are considered long term survivors, or cures, in the B16 model. The universally accepted cut-off for activity in this model, which has been used for years by the NCI, is T/C=125. Conventional use of B16 over the years has set the following levels of activity: T/C<125, no activity; T/C=125–150, weak activity; T/C=150–200, modest activity; T/C=200–300, high activity; T/C>300, with long term survivors excellent, curative activity.

Statistics are performed on the data using primarily the log rank p-value test.

P388 Leukemia

This test is conducted in exactly the same way as the B16 test. The tumor inoculum is prepared by removing ascites fluid containing P388 cells from tumored DBA/2 mice, centrifuging the cells, and then resuspending the leukemia cells in saline. Mice receive $1\times10^5$ P388 cells i.p. on day 0.

MX-1 Human Breast Tumor Xenograft

Nude mice are implanted s.c. by trocar with fragments of MX-1 mammary carcinomas harvested from s.c. growing MX-1 tumors in nude mice hosts. When tumors are approximately 5 mm×5 mm in size (usually about ten days after inoculation), the animals are pair-matched into treatment and control groups. Each group contains 10 tumored mice, each of which is ear-tagged and followed individually throughout the experiment. The administration of drugs or vehicle begins the day the animals are pair-matched (day 1).

The doses, route of drug administration and schedule are selected as appropriate for the study in question. If the MTD dose of an agent is not known, it is determined in an initial dosing experiment in non-tumored mice. In a typical experiment, drugs are given at their MTD and ½ MTD doses i.p. on a daily×5 schedule.

The experiment is usually terminated when control tumors reach a size of 2–3 g. Mice are weighed twice weekly, and tumor measurements are taken by calipers twice weekly, starting on day 1. These tumor measurements are converted to mg tumor weight by a well-known formula, and from these calculated tumor weights the termination date can be determined. Upon termination, all mice are weighed, sacrificed, and their tumors excised. Tumors are weighed, and the mean tumor weight per group is calculated. In this model, the mean control tumor weight/mean treated tumor weight×100% (C/T) is subtracted from 100% to give the tumor growth inhibition (TGI) for each group.

Some drugs cause tumor shrinkage in the MX-1 model. With these agents, the final weight of a given tumor is subtracted from its own weight at the start of treatment on day 1. This difference divided by the initial tumor weight is the % shrinkage. A mean % tumor shrinkage can be calculated from data from the mice in a group that experienced MX-1 regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

Statistics are performed on the data using primarily the log rank p-value test.

Protocols for HIV-1 Inactivation Studies

General protocols for the testing of compounds in in vitro antiviral screens are disclosed in the following references:

1) Perez, V. L., Rowe, T., Justement, J. S., Butera, S. T., June, C. H., and Folks, T. M., An HIV-1-infected T cell clone defective in IL-2 production and Ca$^{++}$ mobilization after CD3 stimulation. J. Immunol. 147: 3145–3148, 1991.

2) Folks, T. M., Justement, J., Kinter, A., Dinarello, C., and Fauci, A. S., Cytokine-induced expression of HIV-1 in a chronically infected promonocyte cell line. Science 238: 800–802, 1987.

3) Folks, T. M., Clouse, K. A., Justement, J., Rabson, A., Duh, E., Kehrl, J. H., and Fauci, A. S., Tumor necrosis factor α induces expression of human immunodeficiency virus in a chronically infected T-cell clone. Proc. Natl. Acad. Sci. USA 86:2365–2368, 1989.

4) Clouse, K. A., Powell, D., Washington, I., Poli, G., Strebel, K., Farrar, W., Barstad, P., Kovacs, J., Fauci, A. S., and Folks, T. M., Monokine regulation of human immunodeficiency virus-1 expression in a chronically infected human T cell clone. J. Immunol. 142: 431–438, 1989.

1. Inactivation of cell-free HIV-1

Cell-free HIV-1 stocks are derived from culture supernatants of H-9 human T cells chronically infected with the HTLV-IIIB strain of HIV-1. Other HIV-1 strains including the MN and some African strains may be used later for confirmatory purposes.

a) Cell-free HTLV-IIIB:

Cell-free HIV-1 ($5\times10^5$ to $1\times10^6$ TCID$_{50}$/ml, or median tissue culture infectious dose) is either left untreated, or treated with RPMI 1640 culture medium, or with different concentrations of antivirals for various time intervals at 37° C., or at a temperature to be determined. After incubation, the treated and untreated are added to $5 \times 10^5$ washed and pelleted target MT-4 cells. After 1 h incubation at 37° C., the MT-4 cells are washed three times with RPMI 1604, resuspended in RPMI 1640 supplemented with 15% fetal bovine serum (FBS), and cultured in a 5% $CO_2$ humidified incubator at 37° C. Cell viability is determined on day 7 of culture by the addition of the 3-(4,5-dimethyl-thiazol-2-yl)-2,5-diphenyitetrazolium bromide (MTT) dye, which changes in color in the presence of live mitochondria. All determinations are done in triplicates.

b) Cell-free JR-CSF:

In addition to assessing the effects of antivirals on a lab strain of HIV-1 (HTLV-IIIB), it is also important to determine antiviral effects on a primary isolate of HIV-1 (JR-CSF), which only infects primary human peripheral mononuclear cells (PBMCs). Human PBMCs activated with phytohemagglutinin A (PHA, Sigma Chemical Co.) are prepared by culturing PBMCs in RPMI 1640 culture medium supplemented with 10% FBS (complete medium) and 2.0 μg of PHA/ml for 1 day before used in infectivity studies. HIV-1 (JR-CSF) untreated or treated as above are added to PHA-activated human PBMCs, and incubated for 1 h at 37° C. After incubation, 1.0 ml of complete RPMI 1640 culture medium is added to the cells. Culture supernatants are collected on days 3, 6 and 9 of culture, and the amounts of HIV-1 p24 core protein are determined in triplicate by the HIV-1 p24 antigen capture assay (Coulter Immunology, FL, or NEN-Du Pont, Wilmington, Del.).

2. Inactivation of cell-associated HIV-1

HIV-1-infected human cells to be used include the chronically infected H-9 cells (HTLV-IIIB or MN strains), and human PBMCs infected with HTLV-IIIB or with JR-CSF, HTLV-IIIB and MN infected H-9 cell lines are available in our laboratory. For infected human PBMCs, fresh human PBMCs are obtained from normal volunteers and stimulated with PHA, and infected with HTLV-IIIB or JR-CSF, as described above. On day 7 after in vitro infection, infectivity is checked by testing for the presence of HIV-1 p24 in the culture supernatants. Infected cultures are divided in equal aliquots. One set is then treated with antivirals at different concentrations for various time intervals, whereas one set is left untreated. Culture supernatants collected on days 3, 6 and 9 of culture will be assessed for HIV-1 p24 levels by the p24 antigen capture assay kit. Cells from these cultures can also be used in immunofluorescence (IF) studies to determine the percentage of cells expressing HIV-1 antigen(s).

3. Inactivation of HIV-1 latently infected cells

These assays are designed to study the effects of antivirals on HIV-1-latently infected cells. One or more of the following HIV-1 latently infected human cell lines can be used (J1—1, U1/HIV, and ACH-2 obtained from the NIH AIDS Research and Reagent Reference Program, Rockville, Md.). These cells are characterized by HIV-1 infection without significant HIV-1 viral replication unless they are stimulated with different cytokines which results in a 10–100 fold increase in HIV-1 replication. J1—1, or U1/HIV, or ACH-2 cells are seeded in 96-well round-bottom tissue culture plates to give $5 \times 10^5$/well in RPMI 1640 supplemented with 15% fetal bovine serum (FBS). The cells are either left untreated or treated with different concentrations of antivirals for various time intervals. Subsequent to treatment, treated and untreated cells are washed three times in RPMI 1640 and are stimulated as follows.

The J1—1 cells are stimulated with 1000 U of α tumor necrosis factor (α-TNF, Genzyme) for 48 h at 37° C., as previously described (ref.1).

The U1/HIV-1 cells are stimulated with 20%–40% PHA-culture supernatant (Electronucleonics) for 48 h at 37° C. (ref.2). The PHA-sup will either be purchased from Electronucleonics or will be prepared by us. The prepared PHA-sup, normal human PBMC will be cultured at a cell density of $10^6$ cells/ml in RPMI 1640 supplemented with 15% FBS and 10 μg/ml of phytohemagglutinin A (PHA, Sigma Chemical Co.). The culture supernatant will be harvested, filtered through a 2 μm filter and used to stimulate the U1/HIV cells as described above.

The ACH-2 cells will be stimulated by addition of 1.0 μM of phorbal 12-myristate 13 acetate (PMA, Sigma Chemical Co.) for 48 h at 37° C. as described (3,4). At the end of the stimulation period, culture supernatants are collected and HIV-1 expression is assessed by the HIV-1 p24 antigen capture ELISA (Du Pont) and by the reverse transcriptase (RT).

In inactivation of cell-associated HIV-1 experiments, the treated and untreated cells could also be submitted to PCR analysis.

4. Inhibition of HIV-1-induced syncytium formation

HIV-1-infected H-9 cells are left untreated or treated with antivirals as described above. Treated and untreated cells ($5 \times 10^4$ cells/well) are added to 96-well flat-bottom microtiter tissue culture plates containing $1 \times 10^5$ indicator SupT1 human T cells/well in complete RPMI 1640 culture medium. Following overnight incubation at 37° C., syncytium formation is scored by two independent people using an inverted microscope scope.

5. Cytotoxicity studies

The cytotoxicity of the antivirals can be tested on a variety of cell types. All of the cell lines used above and normal human PBMCs are incubated with different antiviral concentrations for various time intervals as described above. Cytotoxicity is determined by the MTT dye method (see above) and by [$^3$H]thymidine uptake and scintillation counting.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodymanic characteristics of the particular active ingredient, and its mode and route of administration; age, health, and weight of the recipient; nature and extent of symptoms; kind of concurrent treatment, frequency of treatment, and the effect desired. Usually a daily dosage (therapeutic effective amount or cancer-inhibiting amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.05–95% by weight based on the total weight of the composition.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules: Capsules are prepared by filling standard two-piece hard gelatin capsulates each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution, U.S.P. and 0.025 millimeters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A compound of the formula:

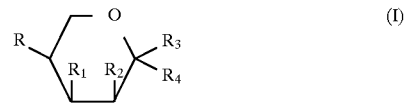

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atomsand n is 2 or 3;

$R_1$ and $R_2$ are independently H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atomsand m is 2 or 3;

$R_3$ and $R_4$ are independently B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine.

2. A compound of claim 1 wherein $R_3$ is defined as B and $R_4$ is H.

3. A compound of claim 1 wherein $R_4$ is defined as B and $R_3$ is H.

4. A compound of claim 1 wherein B is a nucleobase selected from the group consisting of C, T, U, G, A or 5-fluorouracil.

5. A compound of claim 1 wherein R–$R_2$ are each OH.

6. A compound of claim 1 wherein $R_3$ is B; $R_4$ is H; B is a nucleobase selected from the group consisting of C, T, U, G, A or 5-fluorouracil; and R–$R_2$ are each OH.

7. A compound of claim 1 wherein $R_4$ is B; $R_3$ is H; B is a nucleobase selected from the group consisting of C, T, U, G, A or 5-fluorouracil; and R–$R_2$ are each OH.

8. The compound of claim 1 which is selected from the group consisting of β-L-ribopyranosylcytosine, β-L-ribopyranosylguanine, β-L-ribopyranosyladenosine, β-L-ribopyranosyluracil, β-L-ribopyranosyl-5-fluorouracil, and α-L-ribopyranosyl-5-fluorouracil.

9. A pharmaceutical composition comprising a pharmaceutically acceptable carrier and a therapeutically effective amount of a compound of claim 1.

10. A pharmaceutical composition comprising a pharmaceutically acceptable carrier and a therapeutically effective amount of one or more of the compounds of claim 8.

11. A method for treating cancer in a mammal comprising administering to a mammal in need thereof, a cancer-inhibiting amount of a compound of the formula:

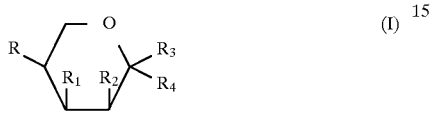

(I)

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atomsand n is 2 or 3;

$R_1$ and $R_2$ are independently H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atomsand m is 2 or 3;

$R_3$ and $R_4$ are independently B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkythio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is b and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine.

* * * * *

(12) EX PARTE REEXAMINATION CERTIFICATE (5188th)
United States Patent
Weis et al.

(10) Number: US 5,885,972 C1
(45) Certificate Issued: Aug. 23, 2005

(54) L-PYRANOSYL NUCLEOSIDES

(75) Inventors: Alexander L. Weis, San Antonio, TX (US); Charles T. Goodhue, Rochester, NY (US)

(73) Assignee: Genencor International, Inc., Rochester, NY (US)

Reexamination Request:
No. 90/005,444, Aug. 24, 1999

Reexamination Certificate for:
Patent No.: 5,885,972
Issued: Mar. 23, 1999
Appl. No.: 08/720,853
Filed: Oct. 2, 1996

Related U.S. Application Data

(63) Continuation of application No. 08/327,932, filed on Oct. 24, 1994, now abandoned.

(51) Int. Cl.$^7$ ............................................. A61K 31/70
(52) U.S. Cl. ............................ 514/45; 514/46; 514/42; 514/47; 514/48; 514/49; 514/50; 514/51; 514/43; 536/4.1; 536/17.2; 536/17.3; 536/18.1; 536/18.4; 536/27.23; 536/27.6; 536/27.8; 536/27.81; 536/28.1; 536/28.53; 536/28.54
(58) Field of Search ............................... 514/25, 45, 46, 514/49, 50, 42, 47, 48, 51; 536/4.1, 17.2, 17.3, 18.1, 18.4, 27.23, 27.6, 27.8, 27.81, 28.1, 28.53, 28.54

(56) References Cited

PUBLICATIONS

Fuertes et al., J. Org. Chem., vol. 40, 2372–2377.*
Fuertes, et al., "Synthesis of Pyrimidine and Purine nucleosides from L–Lyxopyranose and L–Arabinopyranose," J. Org. Chem., V. 40 (16), pp. 2372–2377.
Lin, et al., "Synthesis and Biological Evaluation of 2',3'–Dideoxy–L–pyrimidine Nucleosides as Potential Antiviral Agents against Human Immunodeficiency Virus (HIV) and Hepatitis B Virus (HBV)," J. Med. Chem., V. 37, pp. 798–803, 1994.
Perigaud, et al., "Potential Antiviral Agents. Stereospecific Synthesis of Purines and Pyrimidines Substituted with Chiral Acyclic Chains by Sugar–Ring Opening of α–L–Arabinopyranosyl Nucleosides," J. Chem. Soc. Perkin Trans, V. 1, pp. 1943–1952, 1992.

* cited by examiner

Primary Examiner—Samuel Barts

(57) ABSTRACT

This invention relates to α and β-L-pyranosyl nucleosides of Formula (I), wherein the nucleoside substitution on the pyranosyl carbohydrate molecule comprises a substituted or unsubstituted purine (adenine or guanine) or pyrimidine (cytosine, uracil, thymine and hypoxanthine) base. Also provided are methods to make the α and β-L-pyranosyl nucleosides and methods of using such to treat cancer in a mammal.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 11 is confirmed.

Claims 1–7 and 9 are cancelled.

Claim 8 is determined to be patentable as amended.

Claim 10, dependent on an amended claim, is determined to be patentable.

New claims 12–56 are added and determined to be patentable.

8. [The] *A* compound [of claim 1 which is], *or a pharmaceutically acceptable salt thereof,* selected from the group consisting of β-L-ribopyranosylcytosine, β-L-ribopyranosylguanine, β-L-ribopyranosyladenosine, β-L-ribopyranosyluracil, β-L-ribopyranosyl-5-fluorouracil, and α-L-ribopyranosyl-5-fluorouracil.

*12. A compound of the formula:*

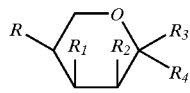

*or a pharmaceutically acceptable salt thereof, wherein:*
*R is $OR_5$ wherein $R_5$ is $H_2$ $COR_6$, or $P(O)_n$ $R_7$ $R_8$ and wherein $R_6$ is substituted or unsubstituted alkyl of 1–5 carbon atoms or a substitued or unsubstituted aromatic ring structure, $R_7$ and $R_8$ are each H or alkyl of 1–5 carbon atoms and n is 2 or 3;*
*$R_1$ is mono-, or di-halogen, or $OR_9$, wherein $R_9$ is H, $COR_{10}$, $P(O)_m$ $R_{11}$ $R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;*
*$R_2$ is H, mono-, or di-halogen, or $OR_9$, wherein $R_9$ is H, $COR_{10}$, $P(O)_m$ $R_{11}$ $R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;*
*$R_3$ is B, H or $OR_{13}$, wherein $R_{13}$ is H, $COR_{14}$, $P(O)_p$ $R_{15}$ $R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and*
*$R_4$ is B, H or $OR_{13}$, wherein $R_{13}$ is H, $COR_{14}$, $P(O)_p$ $R_{15}$ $R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and*
*B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloakylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;*
*provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine.*

*13. A compound of claim 12 wherein $R_3$ is defined as B and $R_4$ is H.*

*14. A compound of claim 12 wherein $R_4$ is defined as B and $R_3$ is H.*

*15. A compound of claim 12 wherein B is a nucleobase selected from the group consisting of C, T, U, G, A or 5-fluorouracil.*

*16. A compound of claim 12 wherein $R$–$R_2$ are each OH.*

*17. A compound of claim 12 wherein $R_3$ is B; $R_4$ is H; B is a nucleobase selected from the group consisting of C, T, U, G, A or 5-fluorouracil; and $R$–$R_2$ are each OH.*

*18. A compound of claim 12 wherein $R_4$ is B; $R_3$ is H; B is a nucleobase selected from the group consisting of C, T, U, G, A or 5-fluorouracil; and $R$–$R_2$ are each OH.*

*19. A pharmaceutical composition comprising a pharmaceutically acceptable carrier and a therapeutically effective amount of a compound of claim 12.*

*20. A compound of the formula:*

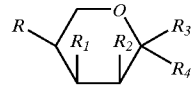

*or a pharmaceutically acceptable salt thereof, wherein:*
*R is $OR_5$ wherein $R_5$ is H, $COR_6$, or $P(O)_n$ $R_7$ $R_8$ and wherein $R_6$ is substituted or unsubstituted alkyl of 1–5 carbon atoms or a substituted or unsubstituted aromatic ring structure, $R_7$ and $R_8$ are each H or akyl of 1–5 carbon atoms and n is 2 or 3;*
*$R_1$ is H, mono-, or di-halogen, or $OR_9$, wherein $R_9$ is H, $COR_{10}$, $P(O)_m$ $R_{11}$ $R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;*
*$R_2$ is mono-, or di-halogen, or $OR_9$, wherein $R_9$ is H, $COR_{10}$, $P(O)_m$ $R_{11}$ $R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;*
*$R_3$ is B, H or $OR_{13}$, wherein $R_{13}$ is H, $COR_{14}$, $P(O)_p$ $R_{15}$ $R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and*

$R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B.

21. A compound of claim 20 wherein $R_3$ is defined as B and $R_4$ is H.

22. A compound of claim 20 wherein $R_4$ is defined as B and $R_3$ is H.

23. A compound of claim 20 wherein B is a nucleobase selected from the group consisting of C, T, U, G, A or 5-fluorouracil.

24. A compound of claim 20 wherein $R–R_2$ are each OH.

25. A compound of claim 20 wherein $R_3$ is B; $R_4$ is H; B is a nucleobase selected from the group consisting of C, T, U, G, A or 5-fluorouracil; and $R–R_2$ are each OH.

26. A compound of claim 20 wherein $R_4$ is B; $R_3$ is H; B is a nucleobase selected from the group consisting of C, T, U, G, A or 5-fluorouracil; and $R–R_2$ are each OH.

27. A pharmaceutical composition comprising a pharmaceutically acceptable carrier and a therapeutically effective amount of a compound of claim 20.

28. A compound of the formula:

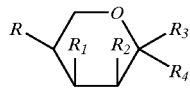

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H of alkyl of 1–5 carbon atoms and p is 2 or 3; and B is a naturally occurring nucleobase selected from the group consisting of A, G, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine.

29. A compound of claim 28 wherein $R_3$ is defined as B and $R_4$ is H.

30. A compound of claim 28 wherein $R_4$ is defined as B and $R_3$ is H.

31. A compound of claim 28 wherein B is a nucleobase selected from the group consisting of T, U, G, A or 5-fluorouracil.

32. A compound of claim 28 wherein $R–R_2$ are each OH.

33. A compound of claim 28 wherein $R_3$ is B; $R_4$ is H; B is a nucleobase selected from the group consisting of T, U, G, A or 5-fluorouracil; and $R–R_2$ are each OH.

34. A compound of claim 28 wherein $R_4$ is B; $R_3$ is H; B is a nucleobase selected from the group consisting of T, U, G, A or 5-fluorouracil; and $R–R_2$ are each OH.

35. A pharmaceutical composition comprising a pharmaceutically acceptable carrier and a therapeutically effective amount of a compound of claim 28.

36. A compound of the formula:

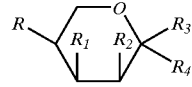

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms of a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that when R and $R_1$ are each OH, $R_2$ is H, and $R_4$ is B, then B cannot be thymine.

37. A compound of claim 36 wherein $R_4$ is defined as B and $R_3$ is H.

38. A compound of claim 36 wherein B is a nucleobase selected from the group consisting of T, U, G, A or 5-fluorouracil.

39. A compound of claim 36 wherein $R$–$R_2$ are each OH.

40. A compound of claim 36 wherein $R_4$ is B; $R_3$ H; B is a nucleobase selected from the group consisting of T, U, G, A or 5-fluorouracil; and $R$–$R_2$ are each OH.

41. A pharmaceutical composition comprising a pharmaceutically acceptable carrier and a therapeutically effective amount of a compound of claim 36.

42. A compound of the formula:

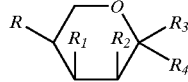

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine.

43. A compound of claim 42 wherein $R_4$ is defined as B and $R_3$ is H.

44. A compound of claim 42 wherein B is a nucleobase selected from the group consisting of T, U, G, A or 5-fluorouracil.

45. A compound of claim 42 wherein $R$–$R_2$ are each OH.

46. A compound of claim 42 wherein $R_4$ is B; $R_3$ is H; B is a nucleobase selected from the group consisting of T, U, G, A or 5-fluorouracil; and $R$–$R_2$ are each OH.

47. A pharmaceutical compisition comprising a pharmaceutically acceptable carrier and a therapeutically effective amount of a compound of claim 42.

48. A compound of the formula:

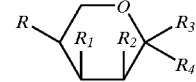

or a pharmaceutically acceptable salt thereof, wherein:

R is $OR_5$ wherein $R_5$ is $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a hetercyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B.

49. A compound of claim 48 wherein $R_3$ is defined as B and $R_4$ is H.

50. A compound of claim 48 wherein $R_4$ is defined as B and $R_3$ is H.

51. A compound of claim 48 wherein B is a nucleobase selected from the group consisting of C, T, U, G, A or 5-fluorouracil.

52. A pharmaceutical composition comprising a pharmaceutically acceptable carrier and a therapeutically effective amount of a compound of claim 48.

53. A compound of the formula:

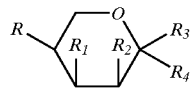

or a pharmaceutically acceptable salt thereof, wherein:

$R$ is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, of di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloakylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine;

wherein $R_4$ is defined as B and $R_3$ is H.

54. A compound of the formula:

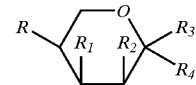

or a pharmaceutically acceptable salt thereof, wherein:

$R$ is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloaklythio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine;

wherein $R–R_2$ are each OH.

55. A compound of the formula:

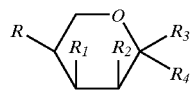

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine;

wherein $R_3$ is B; $R_4$ is H; B is a nucleobase selected from the group consisting of C, T, U, G, A or 5-fluorouracil; and R–$R_2$ are each OH.

56. A compound of the formula:

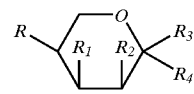

or a pharmaceutically acceptable salt thereof, wherein:

R is $OR_5$ wherein $R_5$ is H, $COR_6$, or $P(O)_n R_7 R_8$ and wherein $R_6$ is substituted or unsubstituted alkyl of 1–5 carbon atoms or a substituted or unsubstituted aromatic ring structure, $R_7$ and $R_8$ are each H or alkyl of 1–5 carbon atoms and n is 2 or 3;

$R_1$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_2$ is H, mono-, or di-halogen, or $OR_9$, wherein $R_9$ is H, $COR_{10}$, $P(O)_m R_{11} R_{12}$ and wherein $R_{10}$ is substituted or unsubstituted alkyl of 1–5 carbon atoms or a substituted or unsubstituted aromatic ring structure, $R_{11}$ and $R_{12}$ are each H or alkyl of 1–5 carbon atoms and m is 2 or 3;

$R_3$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and $R_4$ is B, H or $OR_{13}$, wherein $R_{13}$ is H, $COR_{14}$, $P(O)_p R_{15} R_{16}$ and wherein $R_{14}$ is substituted or unsubstituted alkyl of 1–5 carbon atoms or a substituted or unsubstituted aromatic ring structure, $R_{15}$ and $R_{16}$ are each H or alkyl of 1–5 carbon atoms and p is 2 or 3; and B is a naturally occurring nucleobase selected from the group consisting of A, G, C, U, T, hypoxanthine or a substituted nucleobase comprising one or more substitutions selected from the group consisting of H, halogen, C1–C6 alkyl, C2–C6 alkenyl, C1–C6 alkoxy, C3–C6 cycloalkyl-C1–C6 alkoxy, C3–C8 cycloalkyloxy, C3–C8 cycloalkylthio, C1–C6 alkylthio, aralkylthio, a heterocyclic ring and an aminogroup, provided that when the the nucleobase is a pyrimidine, the atom at position 4 is optionally a sulfur and further provided that when the nucleobase is a purine, the atom at position 6 is optionally sulfur;

provided that only one of $R_3$ or $R_4$ is B and further provided that when R and $R_1$ are each OH, $R_2$ is H, and $R_3$ is B, then B cannot be thymine; and when R and $R_1$ are each OH, $R_2$ is H, and $R_4$ is B, then B cannot be thymine;

wherein $R_4$ is B; $R_3$ is H; B is a nucleobase selected from the group consisting of C, T, U, G, A or 5-fluorouracil; and R–$R_2$ are each OH.

\* \* \* \* \*